United States Patent [19]
Kutsch

[11] Patent Number: 5,865,620
[45] Date of Patent: Feb. 2, 1999

[54] ABRASIVE DENTAL COMPOSITION AND METHOD FOR USE

[75] Inventor: V. Kim Kutsch, Albany, Oreg.

[73] Assignee: Kreativ, Inc., San Diego, Calif.

[21] Appl. No.: 873,526

[22] Filed: Jun. 12, 1997

[51] Int. Cl.$^6$ .................................................. A61G 5/02
[52] U.S. Cl. ............................................. 433/88; 51/309
[58] Field of Search ................................ 433/88; 51/309

[56] References Cited

U.S. PATENT DOCUMENTS

| | | | |
|---|---|---|---|
| 4,494,932 | 1/1985 | Rzewinski | 433/88 |
| 4,867,757 | 9/1989 | Payne | 51/293 |
| 4,950,160 | 8/1990 | Karst | 433/88 |
| 4,956,015 | 9/1990 | Okajima et al. | 51/309 |
| 5,203,698 | 4/1993 | Blake et al. | 433/88 |
| 5,275,561 | 1/1994 | Goldsmith | 433/216 |
| 5,334,019 | 8/1994 | Goldsmith et al. | 433/88 |
| 5,593,467 | 1/1997 | Monroe | 51/309 |
| 5,601,430 | 2/1997 | Kutsch et al. | 433/215 |

OTHER PUBLICATIONS

Goldstein et al; Using Air Abrasive Technology to Diagnose & Restore Pit and Fissure Caries, JADA, vol. 126, Jun. 1995 pp. 761–766.

Kehoe, Bob; Assessing Air Aprasion, Mar./Apr. 1997, Dental Practice & Finance, pp. 40–46.

Rosenberg, S; Air Abrasion: The New Standard of Care, Dentistry Today, Jul. 1996.

Rosenberg, S: Air Abrasion Microdentistry: A New Perspective on Restorative Dentistry, Dental Economics Sep. 1995 pp. 96–97.

Rosenberg, S: Air Abrasive Microdentistry—A New Standard of Care, Focus Jan. 1996.

Kreativ Gammapure Powder ©1996 Kreativ, Inc Sep. 1996.

Primary Examiner—John J. Wilson
Attorney, Agent, or Firm—Lori M. Friedman

[57] ABSTRACT

The invention relates to a process for the effective removal of both hard and soft decay using micro air abrasion dentistry. The process uses a composition which is treated to make it biologically inactive. It comprises at least 95% alumina of a certain particle size distribution and is optimized to remove both hard and soft decay, including carious enamel, carious dentin, stains, calculus, materia alba, organic plug, glass ionomer, composites, resin restoratives, cementum and spent amalgam. Over 50% of the abrasive has particle sizes ranging from 15 to 45$\mu$ with an average particle size of 27.5$\mu$. Other unique features of the abrasive include the addition of color and flavor agents to detect the presence of caries and increase patient enjoyment, respectively.

19 Claims, 4 Drawing Sheets

ABRASIVE DENTAL COMPOSITION AND METHOD FOR USE

BACKGROUND OF THE INVENTION

1. Field of the Invention

The present invention is directed to a process for removing undesirable material from teeth using micro air abrasion dentistry. More specifically, the invention is directed to an abrasive composition used in a process that effectively removes both hard and soft oral materials including carious enamel, dentin, cementum and spent amalgam.

2. Background of the Prior Art

Aluminum oxide or alumina is one of the largest volume pure chemical compounds produced. It is used widely in industrial and commercial applications from abrasives and ceramics to various medicinal compositions and oral preparations, including toothpaste.

In the relatively new field of micro air abrasion dentistry, alumina is a material often used for painless dental procedures. Rosenberg, in the July, 1996 issue of *Dentistry Today* refers to micro air abrasion as the new standard in dental care. This article enumerates many advantages realized in micro air abrasion including increased patient comfort, alleviation of patient anxiety, decreased use of anesthesia, increase of dentists' productivity, and decreased costs to both patients and dentists.

Air abrasion tools have similarly been available for use by dentists for treating patients with an abrasive-laden fluid. Such fluids include abrasive-laden air directed onto the patient's teeth for such procedures as removal of decay, preparing the teeth to receive fillings, prophylactic treatment, and the like. Such abrasion devices provide advantages over conventional dental drills. These include eliminating the heat, noise, and vibration produced by conventional high-speed drills. Also eliminated is the need for anesthesia as well as the need to cool the drill with fluid The early air abrasion micro dentistry materials utilized industrial standard 27 and 50 micron alumina particles. The prior art abrasive materials are not treated for biological purification. Research by applicant has shown that treating the alumina-based abrasive composition for biological inactivity resulted in totally unexpected improvements in its performance in air micro abrasion dentistry.

Using abrasives carried in a fluid stream to remove unwanted oral material is not new. Rzewinski, in U.S. Pat. No. 4,494,932 discloses an air abrasion apparatus and method for cleaning teeth, specifically removing difficult stains and heavy plaque using an unspecified soluble powder. Karst, in U.S. Pat. No. 4,950,160 discloses an air abrasion material for polishing teeth using an unspecified abrasive powder. Other references to the use of the micro air abrasion technique for prophylactic treatment is discussed by Goldstein et al in the Journal of the American Dental Association, Vol. 126, pp 761–766, 1995. In this article, the use of sodium bicarbonate slurry is disclosed to remove stains from teeth.

Goldsmith, in U.S. Pat. No. 5,275,561 discloses a fluid abrasion method for preparing a tooth structure for bonding a composite to the prepared surface using aluminum oxide as the abrasive material. Goldsmith claims a range of particle sizes of alumina ranging from 2 to 100$\mu$. He does not mention any optimum particle size, nor does he mention any distribution of particle size. FIG. 2 shows that the particle size distribution of typical alumina abrasive is very scattered; the data in Table 2 analytically verifies the scattered particle size distribution of the prior art alumina.

A process for the removal of soft tooth decay with an abrasive fluid stream was disclosed by the applicant in U.S. Pat. No. 5,601,430. In this patent, the process uses abrasive particles of a non-toxic thermoset plastic, such as a urea resin, for removing areas of tooth decay and preparing the tooth structure for bonding with a filler material. Applicant was not successful using ordinary alumina in removing soft undesired material such as soft caries.

One of the problems associated with some of the abrasives used in micro air abrasion dentistry is that the same abrasive has traditionally been utilized to cut a multitude of materials. Such materials include both healthy and carious enamel, healthy and carious dentin, cementum, amalgam, composite, glass ionomer, copolymer, cements, porcelain, gold, and other metals.

Traditionally, 'pure' alumina has been used in micro air abrasion dentistry as an abrasive. This material is effective in cutting hard dental materials, including healthy parts of teeth, as well as porcelain and other hard materials listed above. It is, however, less effective on softer materials. Such softer materials that need removal include carious enamel, carious dentin, cementum, spent amalgam, stains, calculus, materia alba, organic plug, composites, resin restoratives, and the like.

The removal of spent amalgam is of particular interest to the dental community. It is comprised of several metals, one of which is mercury, often used for dental restorations. Concern over the efficient and safe removal of these restorations is related to patient exposure to elemental mercury.

In an article in the March/April 1997 issue of *Dental Practice & Finance,* Bob Kehoe authored an article entitled "Assessing Air Abrasion". This article, which is intended to provide advice on the use of micro air abrasion, states that micro air abrasion is "designed to conservatively cut virgin teeth, remove sealants and composite restoration, not amalgam or other metals." In light of this recent assessment, the results of the applicant in removing amalgam with micro air abrasion tools and the composition of the instant invention is quite surprising and remarkable.

Applicant's issued patent U.S. Pat. No. 5,601,430 refers to this fact. In this patent, aluminum oxide is stated to remove hard caries material and healthy tooth structure but to be inefficient in removing soft caries material from decayed tooth structure.

Color has been used previously in certain dental air abrasive systems. In U.S. Pat. No. 5,334,019 Goldsmith et al describe adding fluorescent or colored materials to identify and differentiate between several simultaneously used gas streams. Use of color in the instant invention is for the purpose of caries detection. The use of color in the present invention is also being considered to make the abrasive material easily distinguishable from tooth structure to facilitate clean-up after the dental procedures are completed. Furthermore, since applicant is concerned with only one abrasive stream, use of color in the present application is patentably distinct from the prior use.

It is an object of this invention to provide a process using a micro air abrasion instrument and an abrasive that effectively cuts a variety of soft dental materials, including carious enamel, dentin, cementum, and spent amalgam. It is a farther object of the instant invention to provide an abrasive treated for biological inactivity. Prior art materials used for micro air abrasion have not been so treated. Examples of successful biological treatments include but are not limited to treatment with ethylene oxide, dry heat autoclave sterilization, or gamma radiation.

Microbiological, chemical, and scanning electron microscopic analyses, as will be seen in the Examples, reveal significant differences in purity and particle size distribution between treated and non-treated abrasive materials.

An even further object of this invention is to provide flavored dental abrasive materials. Since anesthetic is seldom used in micro air abrasion dentistry, use of flavored abrasive material would add to the pleasing aspect of the procedure.

Another object is to furnish the abrasive with a dye that would indicate the presence of caries by the development of color. The colorant may also be used to easily distinguish the abrasive particles from the teeth. This would facilitate clean-up after treatment.

The above remarks establish the need in the art for new and improved formulations for micro air abrasion dentistry. The above discussion furthermore emphasizes the uniqueness of the composition and performance characteristics of the instant invention.

SUMMARY OF THE INVENTION

The present invention is directed to a method that effectively removes both hard and soft undesirable dental material including carious enamel, carious dentin, cementum, and spent amalgam and dental debris from the teeth. The method comprises the steps of providing an abrasive composition which is comprised of at least 95% alumina and whose average particle size distribution is at least 50 percent in the range of 15–45 microns.

The composition is subjected to biological treatment rendering it inhospitable to various microorganisms; and has been demonstrated to be especially useful in removing both hard and soft decay, enamel, spent amalgam and other soft dental debris. using the composition with a micro air abrasion dental instrument with standard high volume evacuation. The predominant particle size of the composition of the abrasive is $27.5\mu$.

This process of this invention is performed on patients undergoing micro air abrasion dental treatment for routine dental procedures. It utilizes micro air abrasion dental instruments with standard high volume evacuation equipment.

BRIEF DESCRIPTION OF THE DRAWINGS

A better understanding of the present invention will be had upon reference to the following detailed description when read in conjunction with the drawings in which.

DETAILED DESCRIPTION OF PREFERRED EMBODIMENT

Figure 1:
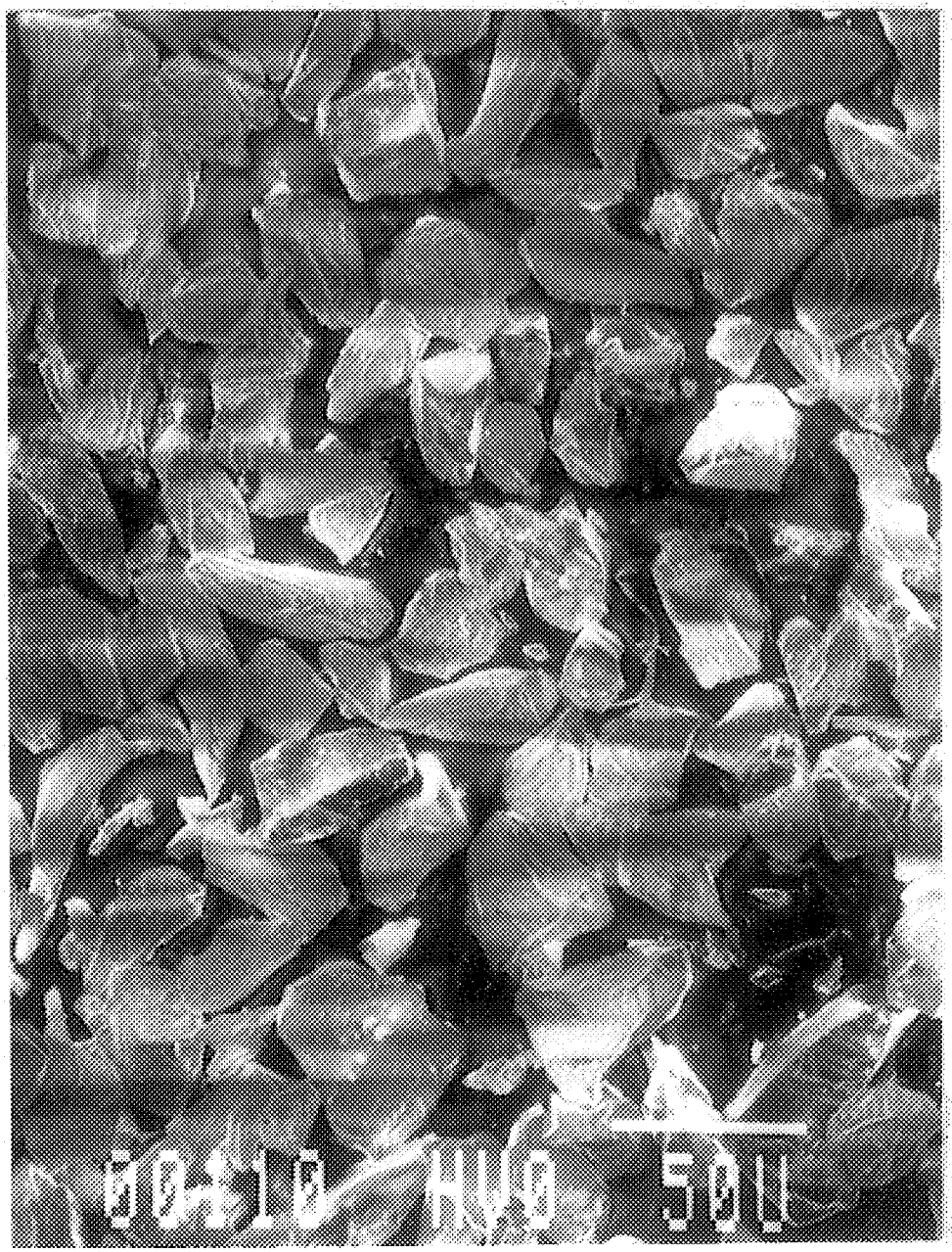
FIG. 1 is a scanning electron photomicrograph illustrating the abrasive particles which are part of the present invention.
Figure 2:
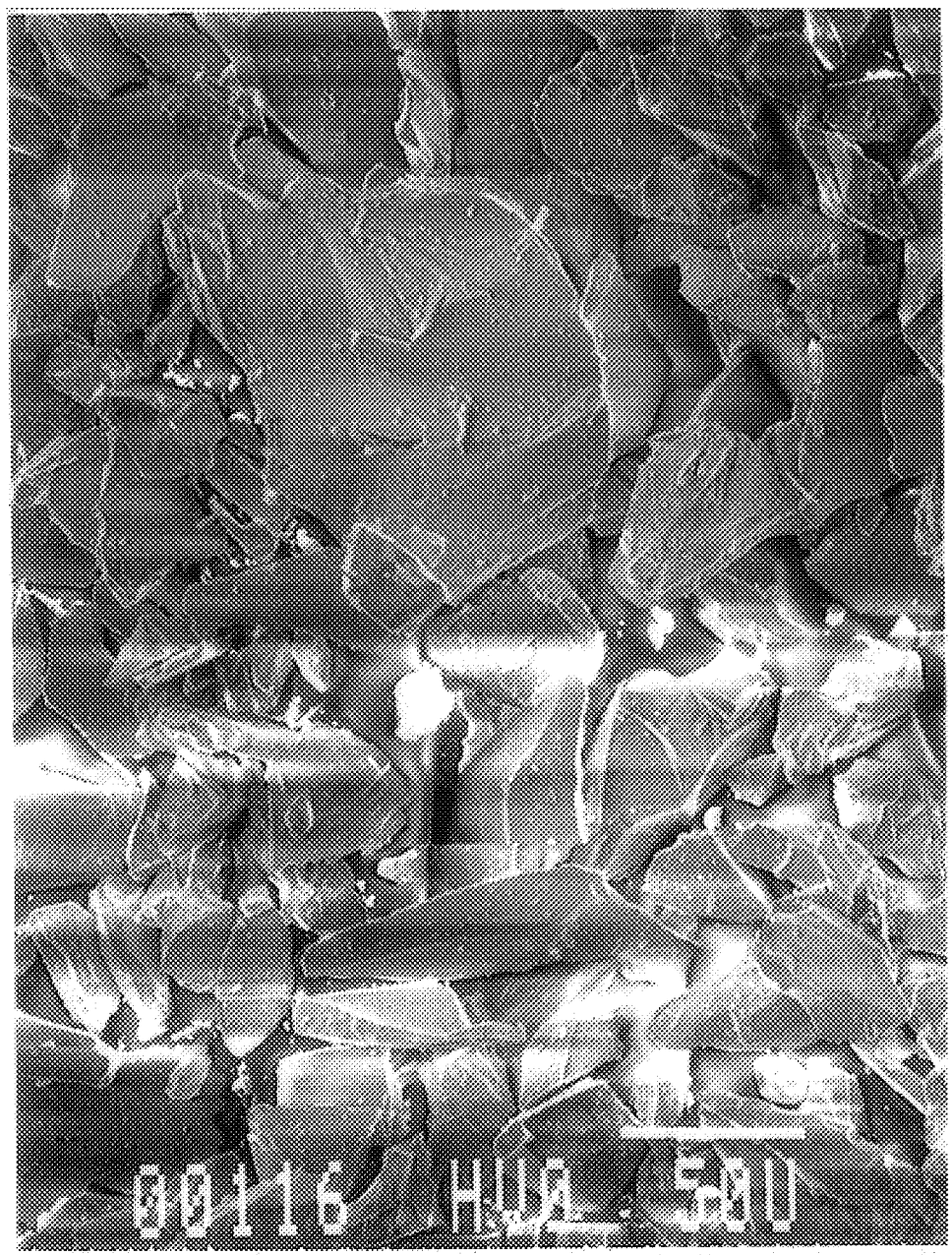
FIG. 2 is a scanning electron photomicrograph illustrating the typical particles of the prior art type of abrasive material.

This invention is directed to a more effective process for removal of unwanted dental material, such as carious enamel, dentin, cementum, spent amalgam, stains, calculus, materia alba, organic plug, composites, resin restoratives and the like. The abrasive composition of this invention is biologically treated for purity and to render it biologically inactive. The alumina so treated resulted in enhanced performance as an abrasive. The optimal particle size of the treated abrasive substance is 27.5 microns. The data relating to particle size distribution, particle shape, texture and analysis of the abrasive of this invention is presented in the Examples section. Reference to FIG. 1 showing regularly-sized particles of the irradiated alumina, is recommended. Comparison to the untreated alumina particles, with greatly different particle sizes, of FIG. 2 is also recommended.

In comparative analyses, the 27.5 micron composition of the instant invention combines high efficiency cutting with maximum patient comfort. The degree of cutting efficiency and patient comfort is surprisingly less if the alumina is labeled having a particle size of 27 microns. Laboratory analyses presented herein also show major differences in particle shape, size, and texture. Particle size distribution of the 27.5 micron abrasive composition of this invention is presented and compared with the 27 micron non-treated pure alumina which is one of the standard prior art abrasives used in micro air abrasion dentistry.

It can see seen from Table 2 in the Examples section that the particle size distribution of the abrasive composition of this invention has over 50% of the alumina particles analyzed to be in the range of 15–45 microns. Table 2 also shows that the prior art alumina, labeled as $27\mu$, has less than 30% of its particles in this size range.

With reference now to FIG. 1, the particles pictured herein are illustrative of the present invention. The particles may be seen as having relatively uniform size and dimensions. FIG. 1 also shows that the individual particles are angular, not smooth. These angular particles contribute to the high cutting efficiency of the abrasive composition of this invention. Clinical results affirm that the 27.5 micron particles provide maximum comfort to the patient.

Referring now to FIG. 2, it can be seen that the particles pictured herein are of alumina furnished for micro air abrasion dentistry labeled as 27 micron in size. It is notable that the particle shape, size, and texture are varied and inconsistent. Various imperfections are seen on the particle surfaces. As can be approximated from the 50 micron measure appearing lower right, some of the particles are quite large. More specifically, some particles of the sample are greater than 50 microns in size.

Figure 3:
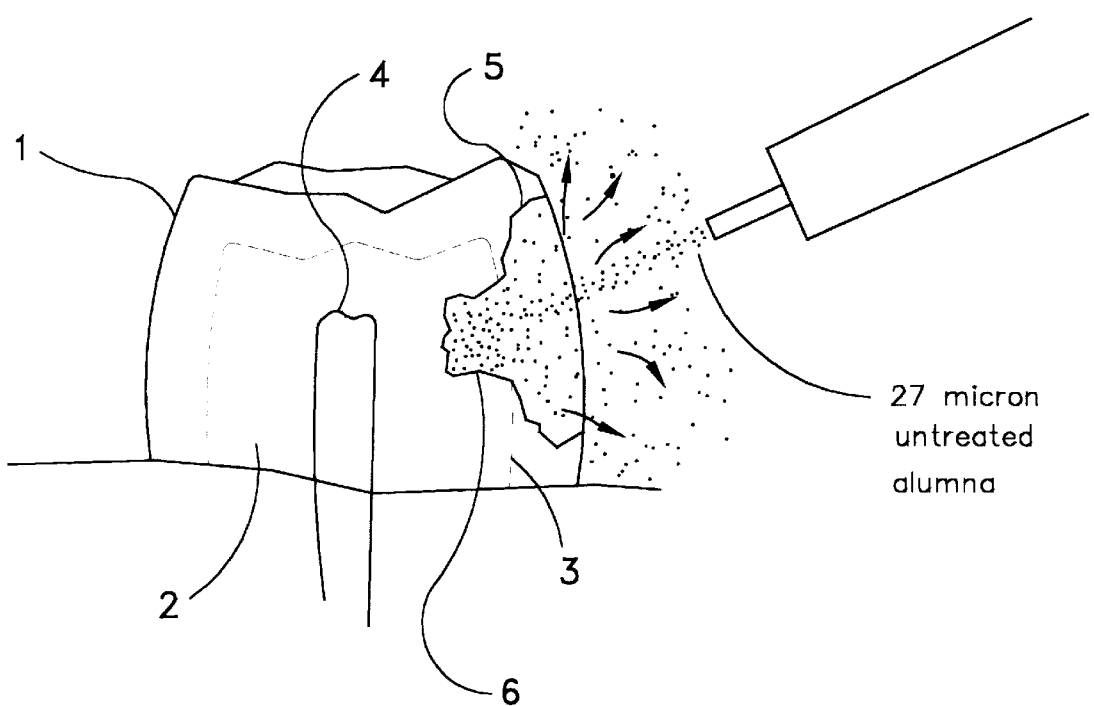
FIG. 3 is a diagram of a cutaway view of a tooth illustrating $27\mu$ untreated prior art alumina attempting to remove decayed enamel and decayed dentin from a tooth.

With reference now to FIG. 3, a cutaway drawing is presented of a decayed tooth undergoing micro air abrasion. In FIG. 3, line 1 is the enamel surrounding the outside of the tooth. The area 2 is the dentin of the tooth, which is inside the enamel closer to the root. The line labeled 3 represents the dentin/enamel junction. The pulp of the tooth, the innermost core of the tooth, is represented by area 4. Areas 5 and 6 represent decayed enamel and decayed dentin, respectively.

FIG. 3 depicts the tooth as the dentist is trying to eliminate both hard decayed enamel and the softer decayed dentin with $27\mu$ untreated alumina of the prior art. It is seen that the particles of this substance do not efficiently penetrate the portion of the cavity that is decayed dentin. The alumina particles are seen to dart in all directions indiscriminately.

Figure 4:
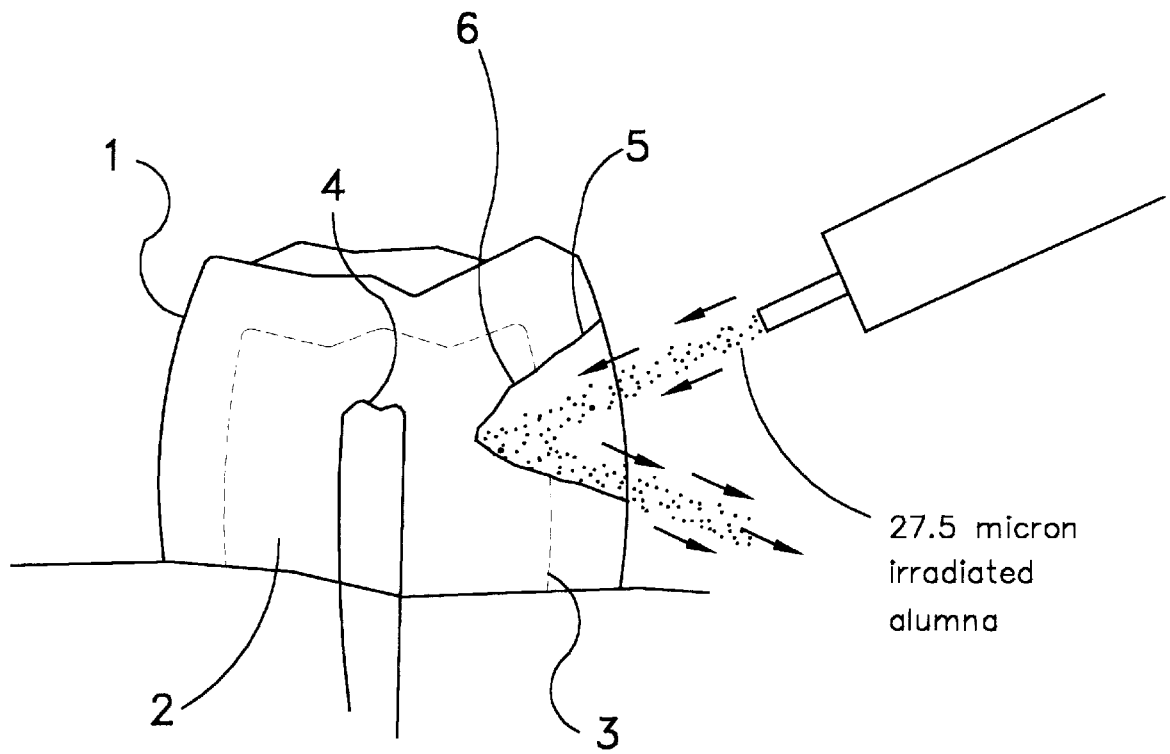
FIG. 4 is a diagram of a cutaway view of a tooth illustrating irradiated $27.5\mu$ alumina of the instant invention successfully removing the decayed enamel and decayed dentin from a tooth.

In FIG. 4, line 1 is the enamel surrounding the outside of the tooth. The area 2 is the dentin of the tooth, which is inside the enamel closer to the root. The line labeled 3 represents the dentin/enamel junction. The pulp of the tooth, the innermost core of the tooth, is represented by area 4. Areas 5 and 6 represent decayed enamel and decayed dentin, respectively. FIG. 4 illustrates irradiated 27.5μ alumina of the instant invention successfully being used to remove decayed enamel and decayed dentin from a tooth. The instant particles can flow smoothly to penetrate the decayed enamel and the decayed dentin to ensure that the caries is removed efficiently so that the tooth can be filled successfully.

Air abrasive instruments that use alumina (aluminum oxide) particles under pressure as a method for removing decay and other dental debris has been a staple of microdentistry since its beginning. As described by Stewart Rosenberg in FOCUS, Dr. Robert Black in the 1940s described equipment that could cut enamel and dentin with abrasive particles forced through a nozzle in a stream of highly compressed air. Since filler materials needed to complete the restoration were unavailable, implementation of the use of air-abrasive micro dentistry was delayed until the 1980s.

When air abrasion is regularly used, many of the problems associated with traditional dental procedures, such as pain, fear, objectionable drill noise and the like is minimized. Besides less patient anxiety, micro air abrasion is advantageous in creating greater bond strength when repairing or resurfacing old composite restorations, removing old composites, porcelain and acrylic repairs, cleaning out crowns for recementation, and re-etching debonded Maryland bridges.

Alumina (aluminum oxide, $Al_2O_3$) has been the traditional material used in microdental air abrasion. Alumina is also used widely in industrial and commercial applications from abrasives and ceramics to various medicinals and toothpaste. The basic alumina used for microdental air abrasion is comprised mostly of aluminum oxide. The color of the different brands of alumina available from various manufacturers may range from white to light brown. Titanium oxide may be added to alumina to impart added whiteness to the alumina. As can be seen from Table 2a in the Examples, the prior art alumina has a large percentage by weight of titania. Specifically, the prior art alumina is over 5% titanium dioxide. As can be seen from the other Tables in the Examples, whiteness does not necessarily correspond to purity or effectiveness of the abrasive alumina composition.

Substances that impart color other than whiteness may be added to the composition of this invention may be added. The reason for this addition would be to detect the presence of caries in the tooth. Another reason for using a distinctive color added to the alumina-based composition would be to easily detect excess or stray particles to be removed. The color additives used for this purpose include those additives that are regulated for food use by the US Food and Drug Administration as listed in Title 21 of the Code of Federal Regulations, 21 CFR. More specifically, certified color additives are listed in part 74 of this code. Still more specifically, the Food Drug and Cosmetic approved colors such as blue#1, violet #2, and green#6 are suitable examples.

It is also possible to add flavor agents to the composition of this invention. Since micro air abrasion dentistry is intended to be a pleasurable experience, the use of flavoring would enhance this aspect. These flavoring agents may comprise those selected for use and approved by the US Food and Drug Administration. In addition, the flavoring agents contemplated for use in this invention may be among those that are recognized as generally safe by the Flavor Extract Manufacturers Association.

It is noteworthy that abrasives used widely in the field of micro air abrasion are labeled "alumina". Typically, chemical composition and assay are not specified, and these competitive materials are labeled only with respect to particle size. These compositions are not irradiated or otherwise treated for biological inactivity.

It has been stated that one of the problems associated with micro air abrasion in dentistry is that typically one abrasive is used to cut a multitude of materials. Such materials include both healthy and carious enamel, dentin, stains, calculus, materia alba, organic plug, composites, resin restoratives, cementum, amalgam, composite, glass ionomer, copolymer, other cements, porcelain, gold, and the like.

Traditionally, "pure" alumina in particle size ranging from 27 to 50 microns has been used as an abrasive in micro air abrasion dentistry. These materials are effective on hard materials, including healthy teeth plus some of the metals, itemized above, but less effective on softer materials that require removal in dental treatment such as soft decay or amalgam.

The efficient removal of these softer dental materials is important because of the nature and progression of tooth decay. Enamel is 98% mineral hydroxyapatite and only 2% water. It is considered a hard substance. When caries develops at the outer enamel surface of a tooth, the decay is demineralized enamel.

As the decay progresses further into the tooth, it passes through the dentin/enamel junction. Further decay occurs in the dentin layer of the tooth. The dentin is comprised of about 80% organic material, which is relatively soft and about 20% mineral, which is comparatively hard. Compared to the composition of enamel, the carious dentin is softer than carious enamel.

The ability to eliminate soft decay is extremely important to the restorative dental procedure. As the caries progresses into the tooth, not only is the decayed material softer, but it is more hazardous to the tooth and thus extremely important to remove. Traditional abrasive alumina used in micro air abrasion dentistry has been unable to remove the softer material. There is a need in the field of micro air abrasion dentistry to efficiently remove this type of softer decay.

Another softer material of particular interest is the removal of spent dental amalgam. The removal of old amalgam is of particular interest to dental practitioners. One reason for the high level of interest is that a very large percentage of the population has amalgam restorations. A large proportion of the population today are adults who were born in the 1950s. At that time, before widespread fluoridation of water, children had cavities more often. These cavities were almost always filled with amalgam. After 40+ years, these children are now adults who need the old amalgam filings replaced.

Amalgam is comprised of several metals, one of which is mercury, often used for dental restorations. Concern over the efficient and safe removal of these restorations is related to patient exposure to elemental mercury.

Traditionally, this procedure has been done with a traditional high speed drill accompanied by water spray and high volume evacuation. Prior attempts at removing amalgam with micro air abrasion has been neither efficient nor practical. If aluminum oxide is used as the abrasive material, there is concern with excessive cavitation around the amalgam, a loss of precision, and a loss of energy with reflected particles. The abrasive composition of the instant invention has been shown to be clinically effective in amalgam removal as compared to plain alumina. More specifically, the abrasive of this invention, when used with certain combinations of spray nozzles and micro air abrasion pulse parameters, effectively removes spent amalgam. The examples section of this disclosure will report and differentiate between these methods.

A distinct advantage of the alumina-based composition of the invention is its treatment with sterilization techniques. This treatment entails passing the alumina-based composition through gamma radiation or another method of biological treatment. These treatments include but are not limited to treatment with ethylene oxide, dry heat autoclave sterilization, or gamma radiation. Analyses, as presented later, reveal significant differences in purity and particle size distribution between biologically treated and non-treated microdental abrasives.

Gamma radiation and 100% ethylene oxide (EtO) are the predominant techniques utilized for health care product sterilization. Treatment by these means is a cost-effective and efficient way to achieve a high level of purity. More specifically, treatment by the use of cobalt-60 has been used to gamma-irradiate the alumina-based composition of the instant invention. An advantage of the use of this irradiation process is the thorough penetration by the gamma rays through the prepackaged abrasive composition. Since the abrasive material is treated while the alumina is in hermetically sealed packages it adds to the assurance that the material remains purified until used in the dental operatory. Another advantage of the use of gamma irradiation is that no chemical residue is left on the alumina composition as a result of the irradiation.

Irradiation provides treatment with gamma radiation to kill unwanted bacteria and/or reduce microbiological counts. Containers of packaged abrasive are sent to a facility that is dedicated to the treatment of irradiating medical products. The unprocessed material is transferred through a chamber in conveyor totes or carriers. They are then penetrated by gamma rays where the specified dose is transmitted to the packaged alumina containers.

Microbiological testing has shown that the radiation treatment is storage stable for about a year. If a dental practice uses micro air abrasion regularly, their supply of abrasive would be exhausted in significantly less time. Therefore the shelf life of treated abrasive is not a cause for concern to the practitioner who uses the abrasive composition of this invention.

One of the concerns of many dental practitioners and patients is the safety of micro air abrasion. More specifically, the fear of infection is a common worry. If the alumina is treated with gamma radiation for the elimination of microbiological contaminants and assorted unwanted bacteria, these fears are eliminated.

During many dental procedures, the tooth tubules are open and exposed. When open, any bacteria present in the mouth can enter the tooth. If this occurs, pulpal necrosis can occur which could cause death of the tooth. Sensitivity or pulpal inflammation can also occur at this time. If there are cuts in the gum tissue of the patient's mouth or any sores present, the likelihood of infection is even greater. The instant abrasive solves this problem by avoiding the possibility of infection from untreated abrasive alumina. The prior art untreated alumina does not.

Aluminum oxide, or alumina (CAS #1344-28-1) has a hardness of knoop 2000, a density of 3.95 gm/cc and a melting point of 2070 degrees C. Alumina is classified as a refractory oxide. The health hazards resulting from the use of alumina in micro air abrasion are minimal. In a worst case scenario of a one-minute patient exposure to alumina, three grams of alumina is dispensed. The eight hour time weighted average of the total dust that that the patient is exposed to is 6.25 mg. This is less than half of the PEL (permissible Exposure Limit) of 15 mg/m$^3$ permitted by OSHA.

The following examples are intended to be illustrative of the scope and spirit of the instant invention. These embodiments will make apparent to those skilled in the art, other embodiments and examples within the scope of the present invention. This invention should therefore be limited only by the appended claims.

EXAMPLES

Example One and Comparative Example A:

Microbiological Analysis and Comparison of the Composition of the Instant Invention (Kreativ's GammaPure™ and the prior art Alumina (alumina, labeled "KCP Alpha Alumina 27" from American Dental Technologies)

Procedure: One gram of each sample was weighed out and suspended in one hundred milliliters of sterile water. A uniform suspension was made by shaking the mixture. One ml of this suspension was inoculated onto a whole plate of Sheep Blood Agar and a whole plate of MacConkey Agar. Both plates were incubated at 35° C.. for three days, or 72 hours. Two whole plates of Sabouraud Dextrose Agar were also employed for this study. One of them was incubated at 35° C. and the other was incubated at room temperature for 3 days.

The plates were examined at 24 and 72 hours. The final number of colony-forming units on each plate was determined on the third day and a gram stain of the colonies was performed. The final report indicates the number of colony-forming units of each bacterial type, including the gram reaction and bacterial morphology, or yeast per ml of 1:100 dilution of the suspension after 72 hours of incubation.

Results: Sample 1: 27.5$\mu$ Composition of this invention, Gamma-irradiated to eliminate biological contamination Sample 1 was found to have no colony forming units of bacteria or yeast per ml of 1:100 dilution after 72 hours incubation.

Comparative Sample A: 27$\mu$ Untreated alumina for use of as an abrasive for micro air abrasion dentistry.

Comparative Sample A was found to be non-sterile. One colony forming unit of gram positive spore-forming bacilli per ml of 1:100 dilution of suspension was found after 72 hours of incubation.

Example Two: Process 2 and Comparative Process B Amalgam Removal with Micro Air Abrasion and the Composition of this Invention, and Comparative Process B:; Amalgam Removal with High Speed Drill.

The process of this invention (Process 2) and Comparative Process B were designed with two testing situations. These situations were in-vitro using extracted teeth and in-vivo using patients in a clinical setting. Each parameter was tested with the both Process 2 and Comparative Process B using the high speed drill. In each case, data was collected from both processes performed removing the same amalgam restorations. By this is meant half the restoration was removed with micro air abrasion using the process of this invention, and half was removed by Comparative Process B using the high speed drill.

In these examples, old amalgam restorations were selected for removal. It is generally accepted that the mercury content of amalgam restorations decreases with age. The extracted teeth were kept hydrated in saline solution until the measurements were made. For the in-vitro procedures, damp 2×2 cotton sponges were placed in a mannequin to simulate a wet oral environment. The in-vivo measurements involved actual clinical procedures.

Procedures: For Process 2, the micro air abrasive instrument used was the Kreativ Mach 5.0™. The instrument was set at 80 psi, powder flow set at 6.0, PowerPulse mode, with a 0.018 Super sonic handpiece 45° nozzle, and the abrasive composition of this invention, sold as GammaPure™ by Kreativ, Inc. High volume evacuation was provided with standard high volume evacuation (HVE). The extra-oral evacuator used was the Kreativ KleanAir II™, set on high speed at a distance about 8" from the patient/mannequin chin.

The Kreativ KleanAir II™ is an oral vacuum filtration system that captures airborne particles, removes odors and gases, and eliminates airborne biological contaminants. This device has a HEPA filter to remove fine particles, an activated charcoal filter, and is capable of flow of 120 cubic feet per minute (cfm.).

For Comparative Process B, the high speed air turbine handpiece was the Midwest Quiet-Air, set at 60 psi with a Midwest 330 carbide bur. All the conditions were set to reflect actual clinical situations. No rubber dam was used in any of the measurements.

For both Process 2 and Comparative Process B, all mercury measurements were made by the Jerome Model 411 Mercury Analyzer™ from Arizona Instrument. This device is a gold film analyzer that measures electrical resistance across the gold film as a result of the presence of elemental mercury. It reports data in mg/m$^3$ and has a sensitivity level of 0.003 mg/m$^3$. To insure precise measurements, the device was run through the film heat cycle and the bridge balance was set. The mercury analyzer was placed approximately 12" behind and above the patient/mannequin mouth to duplicate the normal breathing zone of the dentist working on the patient. Prior to recording the mercury levels for each parameter, a background elemental mercury measurement in the dental operatory was determined to be 0.000 mg/m$^3$.

Data: The parameters were established and measurements taken and recorded for each. Five measurements were taken in the dental operatory prior to all other measurements, and are listed in Table 1 as measurement 1. Measurements 2–5 used the mannequin set-up with extracted teeth. Measurements 6–9 were made with actual patients. Measurement 10 are five background levels in the dental operatory upon completion of the combined amalgam removal measurements.

TABLE 1

Mercury Meusurements of Amalgam Removal Under Various Conditions

| | ←in-vitro measurements→ | | | | ←in-vivo measurements→ | | | | |
|---|---|---|---|---|---|---|---|---|---|
| 1 initial background level | 2 Mach 5.0 HVE | 3 Mach 5.0 HVE KA II | 4 MQA water spray KA II | 5 MQA HVE water spray KA II | 6 Mach 5.0 HVE KA II | 7 Mach 5.0 KA II | 8 MQA HVE KA II | 9 MQA KA II | 10 end background level |
| 0.000 | 0.000 | 0.000 | 0.000 | 0.000 | 0.001 | 0.005 | 0.003 | 0.006 | 0.004 |
| 0.000 | 0.000 | 0.000 | 0.000 | 0.000 | 0.001 | 0.004 | 0.006 | 0.006 | 0.004 |
| 0.000 | 0.000 | 0.000 | 0.000 | 0.000 | 0.002 | 0.003 | 0.005 | 0.004 | 0.004 |
| 0.000 | 0.000 | 0.000 | 0.000 | 0.000 | 0.005 | 0.003 | 0.004 | 0.004 | 0.004 |
| 0.000 | 0.000 | 0.000 | 0.001 | 0.000 | 0.002 | 0.003 | 0.0003 | 0.005 | 0.004 |
| | 0.000 | 0.000 | | | 0.002 | | 0.004 | | |
| | 0.000 | 0.000 | | | 0.003 | | 0.003 | | |
| | 0.000 | 0.000 | | | 0.006 | | 0.003 | | |
| | 0.000 | 0.000 | | | 0.003 | | 0.004 | | |
| | 0.001 | 0.000 | | | 0.003 | | 0.004 | | |
| Process: | 2 | 2 | B | B | 2 | 2 | B | B | |

Notes for Table 1: All measurements are reported in mg Hg/m$^3$
All examples employing the process of this invention (Process 2) use GammaPure ™ as the abrasive Results and Discussion: The micro air abrasion examples shown in Table 1 and labeled as Process 2 were performed using the abrasive composition of this invention. The average breathing zone reading for the in-vitro mannequin set-up with the Kreativ Mach 5.0 micro air abrasion instrument was 0.000 mg/m3, as was the average for the Midwest Quiet Air (MQA) high speed air turbine handpiece. These results were the same whether the HVE was used with or without the Klean Air II (KAII)

The measurements from the mannequin set-up were the same whether the HVE was used with or without the Klean Air II. The measurements from the mannequin set-up were lower than would be expected for either Process 2 of this invention or comparative process B. There is also a large variation in the amount of mercury present in amalgam restorations depending on their initial mercury content, the age and condition of the restorations.

The study was designed to compare the two techniques for amalgam removal on the same restorations, thus eliminating some variation and yielding valid comparative data. In addition, the sensitivity level of the mercury analyzer was only 0.003 mg/m$^3$, which may have been above the threshold exposure for these particular measurements.

The average breathing zone reading for the in-vivo measurements was 0.003 mg/m3 when removing amalgam with the composition of this invention. The average measurement for the comparative process removing amalgam restorations was 0.004 mg/m$^3$. It is noteworthy that the measurements of the two processes were comparable.

Similarly, the measurements taken from both the breathing zone and background levels were comparable. They were also in line with expectations of experienced dental practitioners. During these procedures, the both the breathing zone and background mercury levels were measured at slight increases. All of the measurements are well below all PELs, TLVs, and CLs for elemental mercury exposure from any state or Federal regulatory agency.

It may be concluded that there was no significant difference in the elemental mercury level levels resulting from any of the different parameters when comparing the instant invention with the prior art process of removing spent amalgam dental fillings.

Example Three: Particle Size and Elemental Analysis

Particle size and elemental analysis of the composition of this invention and the prior art abrasive use in micro air abrasion dentistry were performed. Particle count was done by Optical ASTM E20 and Sample digestion by ASTM D4503. Metals were analyzed by the EPA 7000 series.

Results: The particle size analyses were performed by both sieve analysis and microscopy. The smallest available sieve used for these analyses was 45$\mu$. The particle sizes are characterized by ranges that could reasonably be scanned and classified together. The results are presented below in Tables 2 and 2a. In these Tables, Sample 1 is the composition of the instant invention (Kreativ's GammaPure™ and Comparative Sample A is the prior art alumina (alumina, labeled "KCP Alpha Alumina 27" from American Dental Technologies)

TABLES 2 and 2a

Table 2: Particle Size Distribution

| Particle Size ($\mu$) | % by count Sample 1 | % by count Comparative Sample A |
|---|---|---|
| 5–15 | 5.9 | 13.7 |
| 15–25 | 50.4 | 28.2 |
| >45 | 43.7 | 58.1 |

Table 2a: Chemical/Elemental Analysis

| Analysis (% by weight) | Sample 1 | Comparative Sample A |
|---|---|---|
| Aluminum (Al, as $Al_2O_3$) | 97.6 | 91.6 |
| Copper (Cu, as CuO) | 0.01 | 0.12 |
| Lead (Pb, as PbO) | 0.02 | 0.03 |
| Iron (Fe, as $Fe_2O_3$) | 0.46 | 0.64 |
| Magnesium (Mg as MgO) | 0.30 | 0.38 |
| Manganese (Mn, as $MnO_2$) | 0.01 | 0.04 |
| Potassium (K, as $K_2O$) | 0.08 | 0.25 |
| Silicon (Si, as $SiO_2$) | 1.4 | 1.3 |
| Titanium (Ti, as $TiO_2$) | 0.13 | 5.6 |

As can be seen in the data presented above, combined with FIGS. 1 and 2, the composition of this invention has a much smaller particle size distribution than the prior art abrasive. The particle count data for the instant composition has more than half of its particles in the desired range of 15–45 microns. In contrast, the prior art composition has 28.2% in this size. It is noted that the products are labeled 27.5$\mu$ and 27$\mu$, respectively.

Regarding chemical analysis, the composition of this invention has a combination of small amounts of other metal oxides, most notably iron, magnesium, and silicon. Over 97% of the composition is $Al_2O_3$. The Comparative Sample is less than 92% alumina, and has a relatively large amount of titania, $TiO_2$. It is noteworthy that titanium dioxide is a whitening ingredient and to impart whiteness to alumina.

What is claimed is:

1. A composition comprising at least 95% alumina biologically treated to render the alumina inhospitable to microorganisms, at least 50 percent of the alumina having an average particle size in the range of 15–45 microns.

2. The composition of claim 1 wherein the biological treatment is exposure to ethylene oxide.

3. The composition of claim 1 wherein the biological treatment is autoclaving with dry heat.

4. The composition of claim 1 wherein the biological treatment is gamma radiation.

5. The composition of claim 1 wherein the predominant particle size of the alumina is 27.5 microns.

6. The composition of claim 1 including a coloring agent, a flavoring agent, or both.

7. An hermetically sealed package holding a composition comprising at least 95% alumina, at least 50 percent of the alumina having an average particle size in the range of 15–45 microns, the package being biologically treated to render the alumina inhospitable to microorganisms.

8. The package of claim 7 wherein the biological treatment is exposure to ethylene oxide.

9. The package of claim 7 wherein the biological treatment is autoclaving with dry heat.

10. The package of claim 7 wherein the biological treatment is gamma radiation.

11. The package of claim 7 wherein the predominant particle size of the alumina is 27.5 microns.

12. The package of claim 7 wherein the composition includes a coloring agent, a flavoring agent, or both.

13. A method that effectively removes both hard and soft undesirable dental material including carious enamel, carious dentin, cementum, stains, calculus, materia alba, organic, plug, composites, resin restoratives, glass ionomer, spent amalgam, the method comprising providing an abrasive composition comprising at least 95% alumina biologically treated to render the alumina inhospitable to microorganisms, at least 50 percent of the alumina having an average particle size in the range of 15–45 microns, and creating a fluid including the abrasive composition, the fluid being applied to both the hard and soft undesirable dental material.

14. The method of claim 13 wherein the biological treatment is exposure to ethylene oxide.

15. The method of claim 13 wherein the biological treatment is autoclaving with dry heat.

16. The method of claim 13 wherein the biological treatment is gamma radiation.

17. The method of claim 13 wherein the predominant particle size of the alumina is 27.5 microns.

18. The method of claim 13 the composition includes a coloring agent, a flavoring agent, or both.

19. A method for removing spent amalgam from a tooth, the method comprising providing an hermetically sealed package holding a composition comprising at least 95% alumina, at least 50 percent of the alumina having an average particle size in the range of 15–45 microns, the package being biologically treated to render the alumina inhospitable to microorganisms, and removing the composition from the package and creating a fluid including the abrasive composition, the fluid being applied to the spent amalgam.

* * * * *